Figure 1:
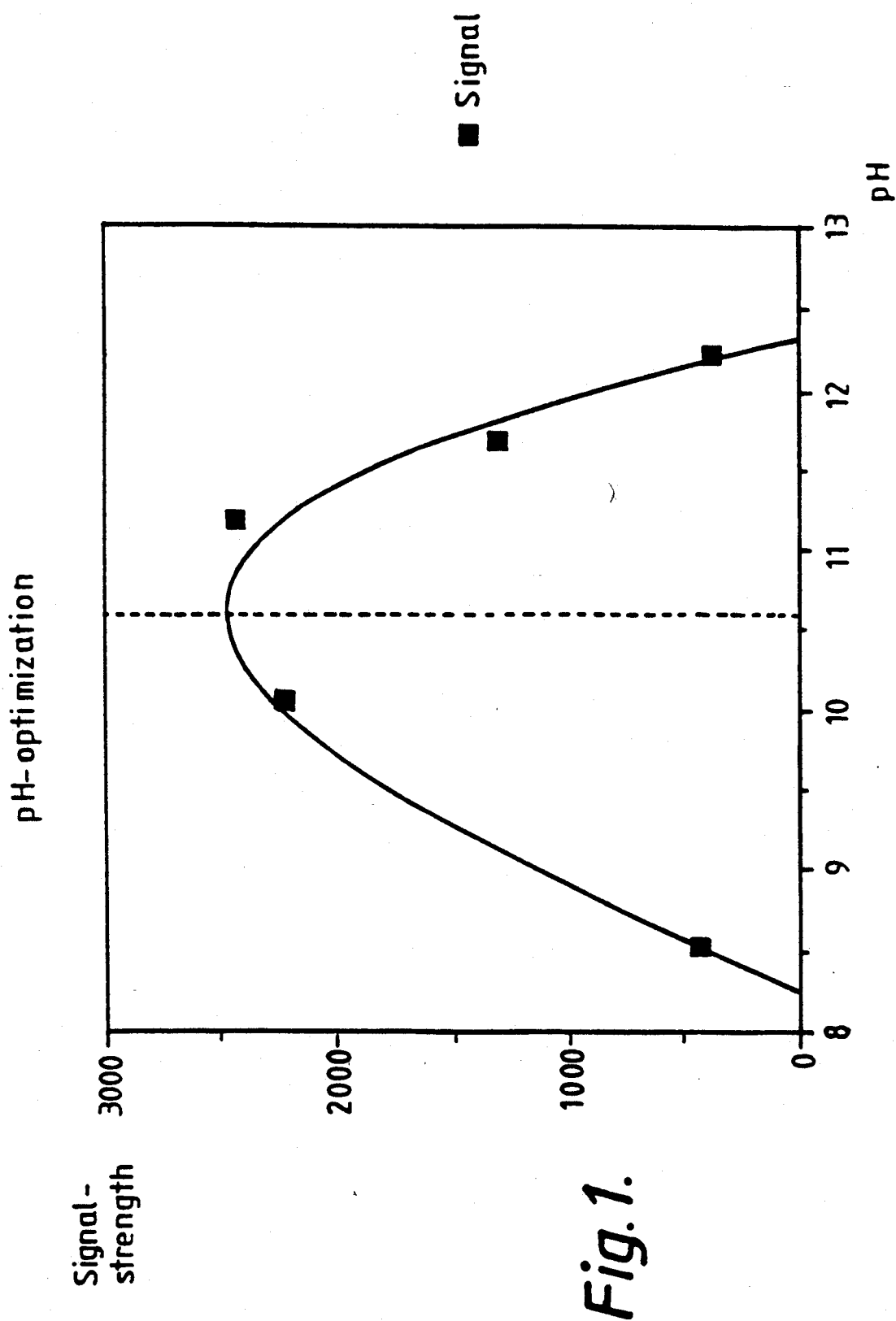

United States Patent [19]
Blomberg et al.

[11] Patent Number: 5,114,841
[45] Date of Patent: May 19, 1992

[54] LUMINESCENT OR LUMINOMETRIC ASSAYS

[76] Inventors: Fred Blomberg, Illersstigen 22, S-171 Solna; Jan Friberg, Meijerfeldts väg 3, S-183 50 Täby; Jan-Olof Glindre, Gränsholmsbacken 16, S-127 42 Skarholmen; Jarl Kangasmetsä, Ostermalmsgaten 84, S-114 50 Stockholm, all of Sweden

[21] Appl. No.: 602,280
[22] PCT Filed: May 11, 1989
[86] PCT No.: PCT/GB89/00512
 § 371 Date: Jan. 9, 1991
 § 102(e) Date: Jan. 9, 1991
[87] PCT Pub. No.: WO89/11103
 PCT Pub. Date: Nov. 16, 1989

[30] Foreign Application Priority Data

May 12, 1988 [EP] European Pat. Off. .......... 8811294.1

[51] Int. Cl.$^5$ .............................................. C12Q 1/28
[52] U.S. Cl. ...................................... 435/7.9; 435/7.1
[58] Field of Search ............... 435/7.1, 7.9, 968, 28; 436/172, 805

[56] References Cited

U.S. PATENT DOCUMENTS 4,598,044  7/1986  Kricka et al. ......................... 435/28
4,729,950  3/1988  Kricka et al. ................... 435/810 X

*Primary Examiner*—Sam Rosen
*Attorney, Agent, or Firm*—Pollock, Vande Sande & Priddy

[57] ABSTRACT

A luminescent or luminometric assay procedure involving a two-step reaction. In the first step a reaction takes place between a selected oxidant, an enzyme for catalyzing oxidation reactions of that oxidant, and a substrate for that enzyme, resulting in an intermediate product which is a sufficiently-powerful oxidizing agent to bring about luminescent oxidation of a chemiluminescent DPD. In the second step, that intermediate compound is reacted with DPD resulting in a brief and relatively intense emission of light. An assay kit to facilitate the carrying out of this assay procedure.

11 Claims, 3 Drawing Sheets

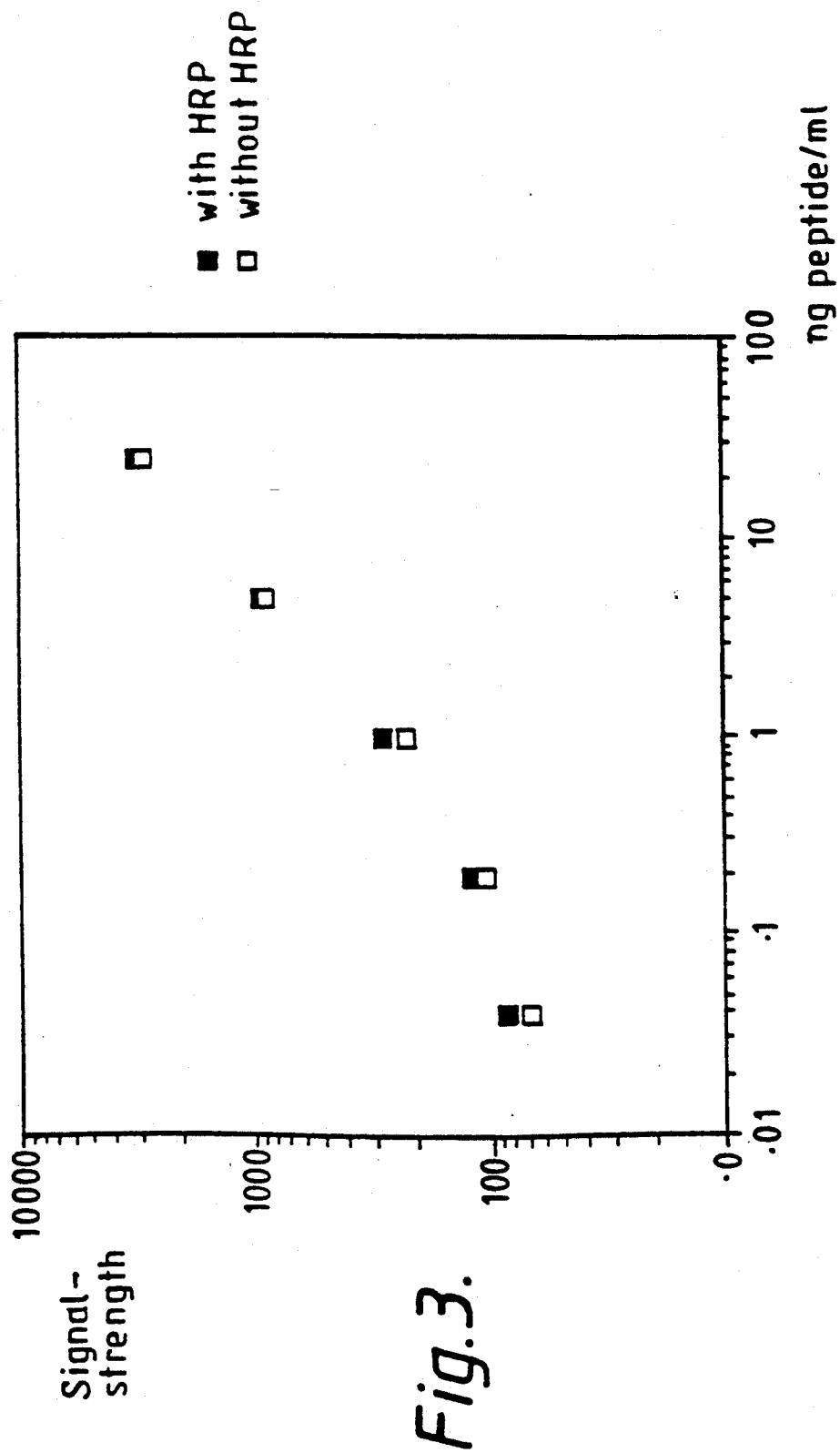

LUMINESCENT OR LUMINOMETRIC ASSAYS

This invention relates to improvements in luminescent or luminometric bioaffinity assays, for example immunoassays, and to diagnostic kits whereby such assays can be readily performed.

An immunoassay enables the detection of an analyte which may be an antibody or an antigen. An antigen may be detected by using an antibody which is specific to that antigen. Alternatively, immunoassays can be used to determine antibodies by utilizing their specific binding to a particular antigen. At first, either antibodies or antigens were covalently linked to radioactive atoms which acted as labels enabling quantitative detection of the labelled component in the resulting antigen/antibody complex. However, radioactive detection systems suffer from a number of important disadvantages. For example, the radioactive agents required are inherently hazardous and can present problems of disposal. Further, as the radioisotopes normally used have a relatively-short half life, they can be stored for only limited periods. These isotopes are also expensive.

Partly as a result of these and other disadvantages of using radioactivity as a label in immunoassay systems, certain alternative detection systems have been developed. Some of these systems utilize as labels compounds that can take part in chemical reactions which result in the emission of light. The light emitted by the reaction can be quantitatively measured to give an accurate estimate of the amount of labelled immunoreactant bound which reflects the amount of analyte present in the sample, enabling it to be quantitatively measured by the assay.

One type of luminescent immunoassay is based on the reaction between a per compound as oxidant (e.g. hydrogen peroxide), a peroxidase catalyst, and a luminescent 2,3-dihydro-1,4 phthalazinedione (herein abbreviated to DPD), in which the peroxidase can act as the label.

Various modifications and improvements of the above-mentioned luminescent system have been proposed. For example, GB-A-2162946 (National Research Development Corporation), EP-A-116454 and EP-A-87959 (Secretary of State for Social Services) disclose the use of certain specifically-defined aromatic compounds as so-called "enhancers" of the chemiluminescence resulting from the above reaction. One of the enhancers mentioned in GB-A-2162946 is 3,3',5,5'-tetramethylbenzedine (commonly referred to as TMBZ). Another is N,N,N',N'-tetramethylbenzidine (NNNN-TMBZ). In the reactions described in the above patent applications light emission rises rapidly to a maximum intensity value, which persists for a considerable length of time as a constant or "plateau" value, for example for several minutes. One possible advantage of constant emission of light over an extended period is that the chemical reaction can be carried out outside the luminometric apparatus and then transferred to that apparatus for measurement when emission of light is already taking place. On the other hand, extended light emission can be disadvantageous in certain circumstances. Thus, if a series of test reactions is being carried out in the wells of a conventional microtiter plate, and if as a result of extended photoluminescence several of the wells contain glowing reaction mixture at the same time, there is a danger of "cross-talk" between two or more wells. In other words, there is a danger of stray light from one or more adjacent wells interfering with the measurement of the luminescence that is being carried out on the contents of a particular well.

It is to be noted that in the assay procedure described in the above patents, the reaction between the peroxidase, the oxidant, the chemiluminescent DPD and the specific aromatic enhancer is carried out in a single step.

We have now discovered that if an aromatic substrate, which may be one of the "enhancers" that can be used in the assay procedures disclosed in the above-mentioned patent applications, the peroxidase and the per compound are reacted together in a first step, an intermediate product is obtained, and that subsequent addition of the DPD at an appropriate pH in a second step results in emission of light of greatly increased intensity, of very short duration, and which rises very rapidly to its peak value. For example, the signal may rise to its peak value in less than 50 milliseconds and return to zero in about two to three seconds.

One preferred substrate for use in the present invention is TMBZ. Where TMBZ is so used, at a sufficiently-high concentration the solution containing the intermediate product obtained in the first stage of the reaction is coloured blue. On the other hand, where NNNN-TMBZ or luciferin (a benzothiazole derivative: 4,5-dihydro-2-6-hydroxy-2-benzothiazolyl)-thiazole-4-carboxylic acid) are used as the substrate, the solution containing the intermediate product is coloured yellow.

The first-step reaction between TMBZ, a peroxidase, and a per compound as oxidant is already known as such in colourimetric assays, as opposed to luminescent assays.

In that case, however, a strong acid is added to the developed blue solution in a second step, resulting in the formation of a yellow solution which is then subjected to colourimetric analysis.

As mentioned above, the reactions disclosed in the above-mentioned patents take place in a single step. We believe that in the reaction mixture a reaction first takes place between the per compound and the so-called "enhancer", catalysed by the peroxidase. We believe that this initial reaction results in the formation of the intermediate product mentioned above, which we believe comprises a free-radical containing compound which is a sufficiently-powerful oxidizing agent to bring about the photoluminescent oxidation of the DPD. We believe that the first step of the reaction is relatively slow, and that the second step is very fast. Thus, it is thought, the intermediate free-radical containing compound is produced relatively slowly, but as it is produced it reacts almost instantaneously with the DPD. Accordingly, the reaction mixture glows for the whole period during which the first reaction step is taking place, and there is essentially no accumulation of intermediate product in the reaction mixture. In our two-step procedure, on the other hand, we believe that the intermediate product accumulates in the reaction mixture whilst the first step of the reaction is being carried out. Then, when we initiate the second step of the reaction by adding the chemiluminescent DPD, all of the accumulated intermediate product reacts essentially instantaneously with the DPD, giving a very short flash of light which is much more intense than the peak achieved in the reactions described in the aforementioned patent specifications.

Thus, as the overall reaction appears to be essentially similar to that disclosed in the above three patent publications, it is to be expected that any of the so-called "enhancers" disclosed in those specifications will be effective in the present invention, provided however that the intermediate product is sufficiently stable to remain until the chemiluminescent DPD is added to initiate the second step of the reaction. It is a matter of simple experiment to determine which of the "enhancers" disclosed in and within the scope of the above patent publications are suitable for use as the aromatic substrate in the present invention.

Certain suitable substrates are aromatic amines, for example TMBZ and NNNN-TMBZ, as already mentioned. Other suitable substrates are benzothiazole derivatives, for example 2,2'-azino bis (3-ethylbenzothiazoline sulfonic acid) (usually known as ABTS) and 4,5 -dihydro-2-(6-hydroxy-2-benzothazolyl)thiazole-4-carboxylic acid (usually known as luciferin). Other possible substrates are phenyl derivatives (e.g. cinnamic acid), halophenols, (e.g. p-iodophenol and substituted phenols (e.g. p-phenyl phenol). All of the above specific examples have been shown to be effective in the present invention.

According to one aspect of the invention we therefore provide a luminescent or luminometric assay which comprises the following steps:

(i) carrying out a reaction between a selected oxidant, an enzyme capable of catalyzing an oxidation reaction utilizing that oxidant, and an aromatic substrate for that enzyme, to obtain an intermediate product which comprises a sufficiently-powerful oxidizing agent to cause luminescent oxidation of a chemiluminescent DPD;

(ii) carrying out a reaction between the intermediate product generated in the first stage and a chemiluminescent DPD, and detecting or measuring the luminescence produced thereby.

Preferably, the selected oxidant is a per compound such as a peroxide, e.g. hydrogen peroxide, in which case the enzyme will be a peroxidase, preferably horseradish peroxidase (herein called HRP).

Because the reaction is carried out in two steps and because only the second step results in the emission of light, accumulation of the intermediate product and thereby amplification of the intensity of luminescence is possible. Moreover the first step may be carried out outside the luminometer that is used to measure the luminescence resulting from the second step. Furthermore, because the luminescence obtained in the second step is of only short duration, a series of reactions may be carried out in the wells of a microtitre plate without the risk of luminescence from surrounding wells interfering with a luminometric measurement being carried out on the contents of a particular well.

As mentioned previously, the enzyme is preferably HRP. It has been found that the catalytic effect of HRP is not affected by pH changes within the range 3.6 to 8.8. The pH for the first step of the reaction is therefore preferably selected within this range to suit the particular substrate that is being used. For example, for TMBZ, the optimum pH has been found to be 5.5.

Where the enzyme is HRP, and the substrate is TMBZ, the incubation temperature for step (i) is preferably about room temperature and the incubation time is preferably about 1 hour. Step (ii) of the reaction, producing the luminescence, is preferably carried out under alkaline conditions, preferably mildly alkaline conditions within the pH range 8.5 to 12, more preferably 10 to 11, and most preferably at a pH of about 10.6.

Thus, another advantage of our two-step assay procedure is that both steps can be carried out at their optimum pH, whereas in a single step procedure as described for example in the above-mentioned patent publications, the chosen pH must be a compromise.

Although hydrogen peroxide is the preferred per compound, perborates have also been used in the invention with success.

Additional per compound, such as hydrogen peroxide, is preferably added with the DPD in step (ii) of the reaction. This is to ensure that an excess of the per compound is present during step (ii) which ensures an optimum luminescent signal.

The preferred luminescent DPDs are luminol and isoluminol. The higher the purity of the DPD used, the better will be the ratio between the luminescent signal and a signal produced by a test blank, i.e. when a test is run in the absence of analyte that can specifically bind the peroxidase-labelled immunoaffinity or bioaffinity reactant.

The assay of this invention has a very wide range of applications and, because of its very high sensitivity, is particularly applicable to the detection of substances occurring at very low concentrations. For example, it may be used to detect the undesirable presence of unwanted cell components in pharmaceutically active polypeptides produced by cells modified by genetic engineering techniques. One such product of major commercial importance is human growth hormone (hGH). Another potential application is in the quantitative detection of human growth hormone occurring in urine samples from individuals with potential growth hormone deficiency. The extremely small quantities of hormone which might appear in urine samples from such individuals demands a particularly efficient assay and the assay procedure according to this invention, where HRP is used as the enzyme, permits the detection of HRP in the atto mole range (i.e. 10-18 moles).

The assay procedure of the invention is applicable to bioaffinity assays other than immunoassals, for example receptor-ligand assays where a particular receptor is collected from cell surfaces and an appropriate ligand is bound to the enzyme.

The component or components of the intermediate product that reacts with the DPD to produce luminescence in step (ii) of the reaction have not been positively identified. However, we have ascertained that the presence of enzyme (e.g. peroxidase) is not required during step (ii). This was established by carrying out step (i) in a microtitration plate well in which the peroxidase had been bound to the inside surface of the well. After step (i) had been carried out the mixture was transferred to a second well, containing no peroxidase, before the addition of the DPD. Luminescence was obtained of essentially the same intensity as was obtained by carrying out step (ii) in the original well with the peroxidase present. If peroxidase had been essential to step (ii), either no luminescence would have been obtained, or allowing for transference of some of the peroxidase of the second well with the intermediate solution, considerably-reduced luminescence would have been expected.

The independence of step (ii) on the presence of HRP was also shown by carrying out the following experiment: HRP contained in a dialysis bag was immersed in a solution of TMBZ and hydrogen peroxide. After incubation the resulting intermediate product was collected from outside the dialysis membrane and used to perform step (ii) of the luminescent reaction.

Normally, of course, steps (i) and (ii) of the reaction will be carried out in the same well.

Because the reaction is a two-step reaction and the luminescence is obtained only in the second step, amplification of the luminescent signal can be obtained by accumulating the intermediate product which is the product of the first step prior to the addition of the chemiluminescent DPD.

The invention will now be illustrated in a non-limiting manner with reference to specific examples and the accompanying drawings, in which:

FIG. 1 is a curve illustrating the optimum pH range for step (i) of the reaction where the enzyme used was HRP. Signal strength (the level of luminosity obtained in step (ii)) is plotted against pH. It will be observed that the optimum pH appears to be about 10.6.

Figure 2:
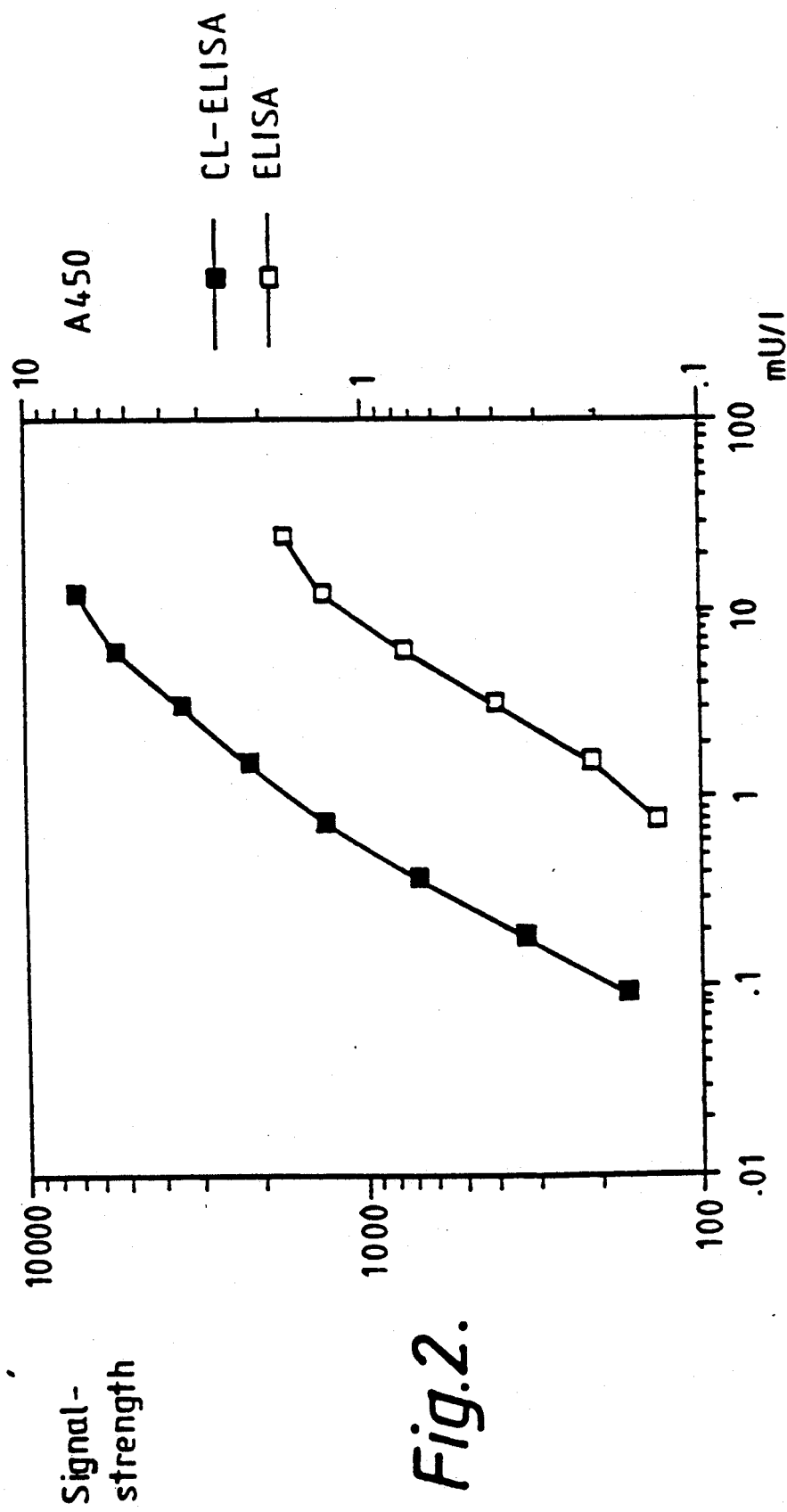

FIG. 2 is a graph comparing the signal strength obtained in the detection of human growth hormone (hGH) obtained using a conventional colourimetric hGH ELISA system, with the chemiluminescent measuring system according to the present invention (identified as CL-ELISA). The colourimetric assay was performed as mentioned above, in which step (i) of the reaction was carried out in the same way as in the present invention, but in which the resulting solution containing the intermediate product was acidified with sulphuric acid to produce a yellow solution which was then analyzed colourimetrically.

The CL-ELISA assay was carried out in accordance with this invention in that the intermediate solution obtained by step (i) was reacted with DPD and further hydrogen peroxide. It can be seen by comparison of the results obtained by the assay procedure of the present invention and the conventional ELISA method, that the chemiluminscent system will yield about a ten-fold increase in detection limited.

FIG. 3 is a graph showing, as mentioned above, that it is not necessary for the enzyme to be present during step (ii) of the reaction. Two sample series were processed identically using the conventional ELISA method, including the substrate incubation step (step (i)). Then, and prior to the chemiluminescent reaction (step (ii)), one of the series of samples was separated from the solid phase enzyme (HRP) by transferring it to a row of empty wells. Step (ii) of the reaction was then carried out and the resulting luminescence measured in the luminometer.

A very small difference in signal strength between the two series can be observed. This very small difference can probably be explained by small losses of liquid during transfer of the solution from one well to another

EXAMPLE 1

An assay for human growth hormone was carried out in accordance with the present invention as follows:

Microtitreplates were first passively coated with affinity-purified rabbit hGH antibodies in carbonate buffer (0.05 mol/l, pH9.6). Thereafter post-coating was performed with 250 μl human serum albumin (hSA, 0.5%) to block all remaining binding capacity on the solid phase surface. After washing away non-bound reagents with washing solution (0.5% Tween 20 and 0.15 mol/l sodium chloride), 100 μl of unknown samples and known references (standards and samples) was added and allowed to incubate for one hour at 37° C.

Thereafter, unbound antigens were washed away with washing solution and a conjugate consisting of Fab' fragments of rabbit anti-hGH antibodies and horseradish peroxidase (HRP) dissolved in sampling buffer (sodium phosphate 0.1 mol/l sodium chloride 0.15 mol/l and human serum albumin 0.5% pH 7.5) was added to the wells of the microtitreplate and incubated for 1.5 hours at 37° C.

Following another washing with the washing solution, to remove excess reagent, the activity of the specifically bound Fab' anti-hGH/HRP conjugate on the solid-phase was quantified by addition of 150 μl of the substrate TMBZ 0.075 g/l in sodium acetate buffer 0.1 mol/l pH 5.5 and 50 μl hydrogen peroxide, 0.02%.

Following the substrate incubation (approximately 45 minutes) the microtitreplate was immediately transferred to a luminometer where the luminescent reaction was started by injection of 126 μl luminol reagent containing luminol 5 mmol/l and further hydrogen peroxide, 0.03%, in Tris-Base 0.4 mol/l. The light signal obtained was recorded by the photodiode-detector. The concentrations of hGH in unknown samples were calculated using linear regression, spline function, logit/-log or any suitable mathematical model allowing acceptable curve-fit over the dilution range.

EXAMPLE 2

An example of an assay kit for human growth hormone in accordance with the invention utilizing HRP-labelled anti-hGH antibodies is as follows:

The kit is used as described in Example 1 and contains the following materials:

a) a microtiter plate coated with immunosorbent purified anti-hGH antibodies.

b) HRP-labelled Fab'-fragments of antibodies to hGH.

c) hGH standard in diluent buffer. Seven prediluted and freeze-dried standards calibrated against the international standard preparation of hGH.

d) Diluent buffer

| | |
|---|---|
| Sodium phosphate | 0.10 mol/l |
| Sodium chloride | 0.15 mol/l |
| Human serum albumin pH 7.5 | 0.5 per cent w/v | e) Serum control.

A freeze-dried human serum with a suitable level of hGH is provided for quality control purposes.

f) Washing solution.

Concentrated solution of,

| | |
|---|---|
| Sodium chloride | 1.5 mol/l |
| Tween 20 | 0.5% v/v |

To be diluted 10 times before use.

g) Substrate buffer.

| | |
|---|---|
| Sodium acetate | 0.1 mol/l |
| Glacial acetic acid pH 5.5 | 800 μl/l | h) Substrate (TMBZ)

| | |
|---|---|
| Stock solution of 3, 3', 5, 5' tetramethylbenzidine in dimethylformamide (DMF) TMBZ | 10 mg/ml | i) Luminescence reagent.

| | |
|---|---|
| Stock solution of luminol in sodiumhydroxide | 0.1 mol/l |
| Luminol | 0.2 g/l | j) Luminescence solvent

| | |
|---|---|
| Tris-Base | 0.4 mol/l | k) Perborate tablet (per compound oxidant)

We claim:

1. A luminescent or luminometric assay which comprises the following steps:
   (i) carrying out an initial reaction between an oxidant containing a peroxy group, a peroxidase, and an aromatic substrate for said peroxidase, to obtain an intermediate product which comprises an oxidizing agent capable of causing luminescent oxidation of a chemiluminescent 2,3-dihydro-1,4 phthalazinedione;
   (ii) and then carrying out a reaction between the intermediate product generated in step (i) above and a chemiluminescent 2,3-dihydro-1,4 phthalazinedione and detecting or measuring the luminescence produced thereby and wherein the light is emitted as a flash with high intensity and short duration and at an effective pH.

2. An assay according to claim 1 in which the substrate is selected from the group consisting of an aromatic amine, a benzothiazole derivative, a phenyl derivative, a halophenol, and a substituted phenol.

3. An assay according to claim 2 in which the substrate is selected from the group consisting of 3,3', 5,5'-tetramethylbenzedine, N,N,N',N'-tetramethylbenzidine, 2,2'-azino bis(3-ethylbenzothiazoline sulfonic acid, luciferin, cinnamic acid, p-iodophenol, and p-phenylphenol.

4. An assay according to claim 1, in which said oxidant is hydrogen peroxide.

5. As assay according to claim 1, in which the peroxidase is horseradish peroxidase.

6. A method according to claim 1 in which said peroxidase is horseradish peroxidase and step (i) is carried out at a pH within the range 3.6 to 8.8.

7. An assay according to claim 6, wherein the substrate is 3,3',5,5'-tetramethylbenzedine and step (i) is carried out at a pH of 5.5.

8. An assay according to claim 6 in which step (ii) is carried out at a pH within the range 8.5 to 12.

9. An assay according to claim 8 in which step (ii) is carried out at a pH within the range 10 to 11.

10. An assay according to claim 9 in which step (ii) is carried out at a pH of about 10.6.

11. An assay according to claim 1 in which the 2,3-dihydro-1,4-phthalazinedione is luminol or isoluminol.

* * * * *